US007939066B2

(12) United States Patent
Puntenney et al.

(10) Patent No.: US 7,939,066 B2
(45) Date of Patent: May 10, 2011

(54) METHODS AND COMPOSITIONS FOR THE INHIBITION OF GROWTH OF INFECTIOUS *ASPERGILLUS FUMIGATUS* AND OTHER MYCOTIC ORGANISMS IN THE GUT OF MAMMALIAN AND AVIAN SPECIES

(75) Inventors: Steven Bruce Puntenney, Independence, OR (US); Neil Elliott Forsberg, Corvallis, OR (US)

(73) Assignee: OmniGen Research, LLC, Corvallis, OR (US)

( * ) Notice: Subject to any disclaimer, the term of this patent is extended or adjusted under 35 U.S.C. 154(b) by 713 days.

(21) Appl. No.: 11/457,176

(22) Filed: Jul. 13, 2006

(65) Prior Publication Data
US 2006/0239992 A1 Oct. 26, 2006

Related U.S. Application Data

(62) Division of application No. 10/388,525, filed on Mar. 17, 2003, now abandoned.

(60) Provisional application No. 60/414,828, filed on Sep. 27, 2002.

(51) Int. Cl.
*A61K 38/47* (2006.01)
*A61K 31/715* (2006.01)
(52) U.S. Cl. ........ 424/94.61; 514/54; 426/656; 426/807
(58) Field of Classification Search ............... 424/94.61; 514/54; 426/2, 656, 807
See application file for complete search history.

(56) References Cited

U.S. PATENT DOCUMENTS

| 3,943,250 A | 3/1976 | Richter et al. |
| 3,961,080 A | 6/1976 | Sugimoto et al. |
| 4,055,667 A | 10/1977 | Linton et al. |
| 4,251,519 A | 2/1981 | Robbins et al. |
| 4,729,902 A | 3/1988 | Urman et al. |
| 4,765,992 A | 8/1988 | Geneix et al. |
| 5,149,549 A | 9/1992 | Beggs |
| 5,165,946 A | 11/1992 | Taylor et al. |
| 5,192,547 A | 3/1993 | Taylor |
| 5,639,492 A | 6/1997 | Turk et al. |
| 5,698,599 A | 12/1997 | Subbiah |
| 5,814,346 A | 9/1998 | Gamberini |
| 5,871,966 A | 2/1999 | Kofod et al. |
| 5,922,373 A | 7/1999 | Johnston |
| 5,935,623 A | 8/1999 | Alonso-Debolt |
| 6,045,834 A | 4/2000 | Howes et al. |
| 6,221,381 B1 | 4/2001 | Shelford et al. |
| 6,344,221 B1 | 2/2002 | Evans |
| 6,476,003 B1 | 11/2002 | Jordan et al. |
| 2002/0048573 A1 | 4/2002 | Klock et al. |
| 2005/0180964 A1 | 8/2005 | Puntenney et al. |
| 2005/0220846 A1 | 10/2005 | Puntenney et al. |
| 2007/0202092 A1 | 8/2007 | Puntenney et al. |
| 2007/0253983 A1 | 11/2007 | Forsberg et al. |

FOREIGN PATENT DOCUMENTS

| DE | 4122906 A1 | 2/1992 |
| EP | 0551331 B1 | 11/1995 |
| EP | 0721741 A1 | 7/1996 |
| JP | 07184595 A | 7/1995 |
| WO | WO 95/30022 A | 11/1995 |
| WO | WO 97/02356 A | 1/1997 |

OTHER PUBLICATIONS

Alexopoulos, C J, Mims, C W, Blackwell, M. Introductory Mycology. 1996. John Wiley & Sons. New York, Chapter 3, pp. 61-85.
AOAC. Official Methods of Analysis of AOAC International. 1997. 16th Edition. vol. 1, , Chapter 4, p. 4 (4.1.10). AOAC Official Method 942.05 Ash of Animal Feed.
Catalano L, Picardi M, Anzivino D, Insabato L, Notar D, Bruno R. 1997. Small bowel infarction by *Aspergillus*. Haematologica vol. 82 pp. 182-183.
Czop, J. K., and K. F. Austen. 1985. A beta-glucan inhibitable receptor on human monocytes: its identity with the phagocytic receptor for particulate activators of the alternative complement pathway. J. Immunol. vol. 134 pp. 2588-2593.
Fontaine T, el al. 2000. Molecular Organization of the Alkali-insoluble Fraction of *Aspergillus fumigatus* Cell Wall. J Biol Chem vol. 275 pp. 27594-27607.
Frosco et al. May 14-18, 1989 Abstract F88, 89th meeting of the American Society for Microbiology, New Orleans, La.
Jaeger E E, Carroll N M, Choudhury S, Dunlop A A, Towler H M, Matheson M M, Adamson P, Okhravi N, Lightman S. Aug. 2000. Rapid detection and identification of *Candida, Aspergillus,* and *Fusarium* species in ocular samples using nested PCR J Clin Microbiol vol. 38(8), pp. 2902-2908.
Jensen H E, Schonheyder H, Basse A. 1991 Acute disseminated *Aspergillosis* in a cow with special reference to penetration and spread. J. Comp. Path. vol. 104, pp. 411-417.
Jensen H E, Aalbaek B, Besse A, Schonheyder H. 1992 The occurrence of fungi in bovine tissues in relation to portals of entry and environmental factors. J. Comp Path. vol. 107, pp. 127-140.
McCausland I P, Slee K J, Hirst F S. May 1987. Mycotic abortion in cattle. Australian Veterinary Journal. vol. 64, No. 5, pp. 129-132.

(Continued)

Primary Examiner — Allison M. Ford
Assistant Examiner — Susan E. Fernandez
(74) Attorney, Agent, or Firm — Klarquist Sparkman, LLP

(57) ABSTRACT

A method for the prevention and treatment of fungal infections and, therefore, consequent invasive mycosis in mammalian and avian species is described. The invention comprises a combination of β-1,3(4)-endoglucanohydrolase, β-1,3(4) glucan, diatomaceous earth, mineral clay, and glucomannan, which is fed to or consumed by mammalian or avian species in amounts sufficient to inhibit enteric fungal colonization in the gut and consequent mycosis. The invention described may be admixed with feeds or foods, incorporated into pelleted feeds or foods or administered orally to mammalian and avian species.

15 Claims, 4 Drawing Sheets

OTHER PUBLICATIONS

Ohsawa H. Feb. 1991. Clinical and pathological analysis of deep mycosis. Kansenshogaku Zasshi. vol. 65(2) pp. 200-208.

Prescott R J, Harris M, Banerjee S S. Sep. 1992. Fungal infections of the small and large intestine. J Clin Pathol. vol. 45(9) pp. 806-811.

Puntenney S B, Wang Y, Forsberg N E. Mycotic infections in livestock: recent insights and studies on etiology, diagnostics and prevention of hemorrhagic bowel syndrome. Proceedings of the 18th Southwest Nutrition and Management Conference, Feb. 20-21, 2003, Phoenix Arizona.

Rhodes J C, Jensen H E, Nilius A M, Chitambar C R, Farmer S G, Washburn R G, Steele P E, Amlung T W. 1992. *Aspergillus* and *Aspergillosis*. Journal of Medical and Veterinary Mycology, vol. 30, Supplement 1, pp. 51-57.

Tomee J F, Kauffman H F. Putative virulence factors of *Aspergillus fumigatus*. Apr. 2000. Clin Exp Allergy vol. 30(4) pp. 476-484.

Xia, Y., V. Vtvika, J. Yan, M. Hanikov, T. N. Mayadas, G. D. Ross. 1999. The B-glucan-binding lectin site of mouse CR3 (CD11b/CD18) and its function in generating a primed state of the receptor that mediates cytotoxic activation in response to iC3b-opsonized target cells. J. Immunol. vol. 162 pp. 2281.

Kessler, G. et al, Glucomannan-protein complexes from cell walls of yeast. 1959. Journal of Biological Chemistry. 234(9);2281-2285.

Magnoli, C et al. The mycoflora and toxicity of feedstuffs from a production plant in Cordoba, Argentina. 2002. Mycotoxin Research 18(1): 177-184.

Tangarone, B. et al. Purification and characterization of an endo-(1,3)-beta-D-glucanase from *Trichoderma longibrachiatum*. 1989. Applied and Environmental Microbiology 55(1):177-184.

Derwent Publications Ltd., London, GB; XP002359382 & RU 2 115 421 C1 (Devichenskii V M) Jul. 20, 1998, abstract.

Derwent Publications Ltd., London, GB; XP002359383 & RU 2 093 162 C1 (AS SIBE Biochem Int) Oct. 20, 1997, abstract.

International Search Report. PCT/US2005/02829. Jan. 16, 2006. pp. 1-4.

Opinion PCT/US2005/02829. Jan. 16, 2006. pp. 1-5.

Proposed Pretrial Order, *Alltech, Inc.* v. *Cenzone Tech, Inc.*, U.S. District Court for the Southern District of California, Civil Action No. 06-CV-0153 JM (RBBx), Jul. 31, 2007.

Civil Docket for Case #: 3:06-cv-00153-JM-RBB, *Alltech, Inc.* v. *Cenzone Tech Inc.*, U.S. District Court, Southern District of California (San Diego), Accessed Sep. 10, 2007.

Information Disclosure Statement, Jun. 18, 2007, filed in reexamination of Patent No. 6,045,834 (Reexamination Control No. 90/008,406).

Information Disclosure Statement, Aug. 16, 2007, filed in reexamination of Patent No. 6,045,834 (Reexamination Control No. 90/008,406).

Information Disclosure Statement, Oct. 29, 2007, filed in reexamination of Patent No. 6,045,834 (Reexamination Control No. 90/008,406).

T.P. Lyons, 1995, Biotechnology in the Feed Industry, Proceedings of Alltech's Eleventh Annual Syposium, Edited by TP Lyons and KA Jacques, Nottingham University Press pp. 1-29.

H.L. Trenholm, L.L. Charmley and D.B. Prelusky, 1996, Mycotoxin Binding Agents:An Update on What We Know, Proceedings of Alltech's Twelfth Annual Symposium, Eds. TP Lyons and KA Jacques, Nottingham, pp. 327-349.

L.L. Charmley, H.L. Trenholm and D.B. Prelusky, 1995 Mycotoxins: Their Origin, Impact and Importance . . . , Proceedings of Alltech's Eleventh Annual Symposium, Edited by TP Lyon and KA Jacques, Nottingham University Press pp. 41-63.

T.F. Savage and E.I. Zakrzewska, 1996, The Performance of Male Turkeys Fed A Starter Diet . . . , Proceedings of Alltech's Twelfth Annual Sumposium, Edited by TP Lyons and KA Jacques, Nottingham University Press, pp. 47-54.

H.L. Trenholm, L.L. Charmely, and D.B. Prelusky, Jan. 1997, Mycotoxin Binding Agents: An Update on What We Know, Zootecnica International, pp. 40-42.

H.J. Peppler, 1979, Production of Yeasts and Yeast Products, Microbial Technology, Microbial Processes vol. 1, 2nd Ed., Academic Press, pp. 157-185.

Product Bulletin, 2000, Bill W. Perkins, Biotech Development Company, Inc., Dexter, Missouri, T-Bind pp. 1-18.

Label, circa 2000, Cenzone Tech, Inc., Microbond.

Specification Sheet, Circa 2000, Cenzone Tech, Inc., A.I.P. Co., Ltd., Microbond, The proven microtoxin absorbent pp. 1-8.

Product Bulletin Cenzone Tech, Inc., Microbond, The Proven Micotoxin Adsorbent that Aids in the Binding and Diminishing the Adverse Effects of Mycotoxins, Dec. 9, 2005, pp. 8-14.

G. Devegowda, Paper presented at African Lecture Tour (Mar. 10-15, 1997), Mycotoxins in Feed, Novel Biotechnological Solutions pp. 1-8.

Product Bulletin, circa 2000, Ciendax S.A. Pronady 500, 100% yeast cell wall (*Saccharomyces cerevisiae*), pp. 1-4.

B.K. Mahesh and G. Devegowda, Apr. 1996, Ability of Aflatoxin Binders to Bind Aflatoxin in Contaminated Poultry Feeds and Liquid Media in vitro, poster presented at Twelfth Symposium on Biotechnology in the Feed Industry.

U.S. Department of Health and Human Services Food and Drug Administration Center for Veterinary Medicine, Oct. 1999, Guidance for Industry, Dioxin in Anti-Caking Agent Used in Animal Feed and Feed Ingredients.

Information Disclosure Statement, Nov. 5, 2007, filed in reexamination of Patent No. 6,045,834 (Reexamination Control No. 90/008,406).

International Search Report and Opinion for PCT/US2007/066968 pp. 1-14 Oct. 8, 2007.

Patil et al, Aug. 2004, Immune response of calves to bentonite and alum adjuvanted combined vaccine . . . Indian Journal of Animal Sciences vol. 74 pp. 845-847.

Wang et al, Identification of the mechanisms by which Omnigen-AF, a nutritional supplement, augments immune function in ruminant livestock. 2004. Proceedings, Western Section, American Society of Animal Science. vol. 55, pp. 349-352.

Chapman et al, Effects of Omnigen AF on milk production and on lactation persistence in a commercial dairy setting, Jul. 2005, Journal od Animal Science vol. 83 (Suppl 1) Abstract T177.

Omnigen AF Product Information at www.omnigenresearch.com/feed.php, Accessed Jan. 27, 2008.

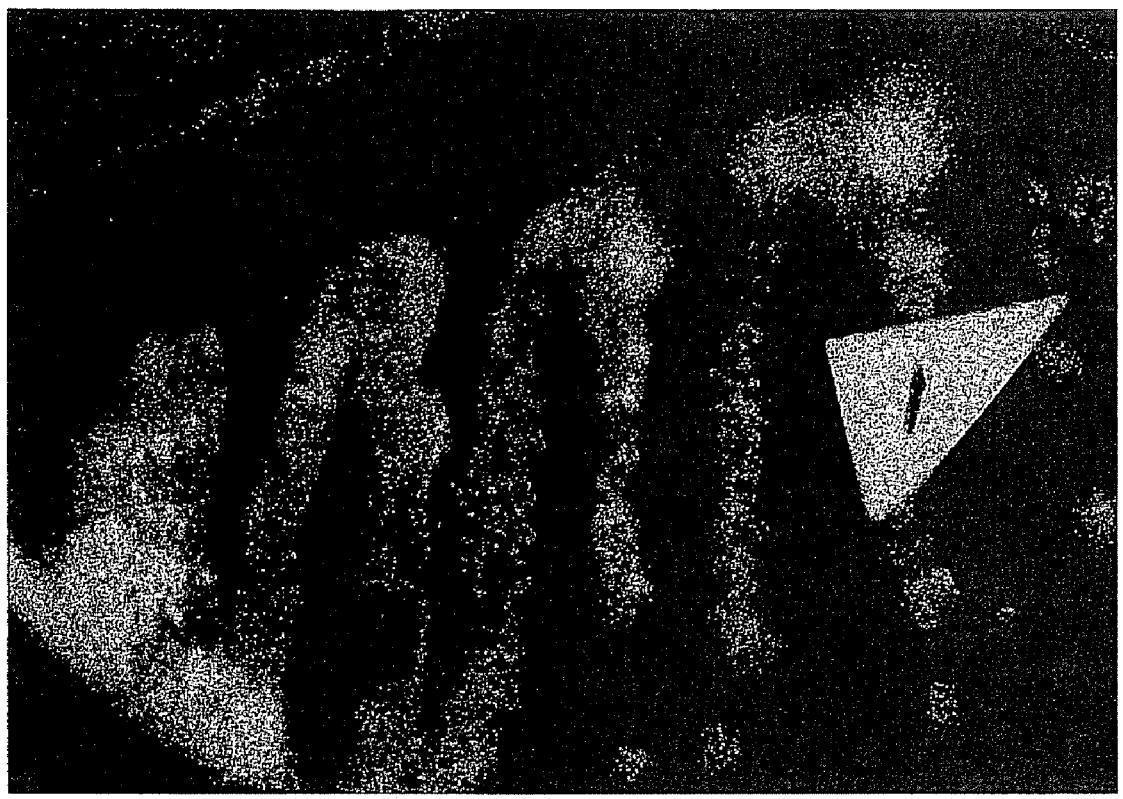
Figure 1, Puntenney and Forsberg

Figure 2, Puntenney and Forsberg
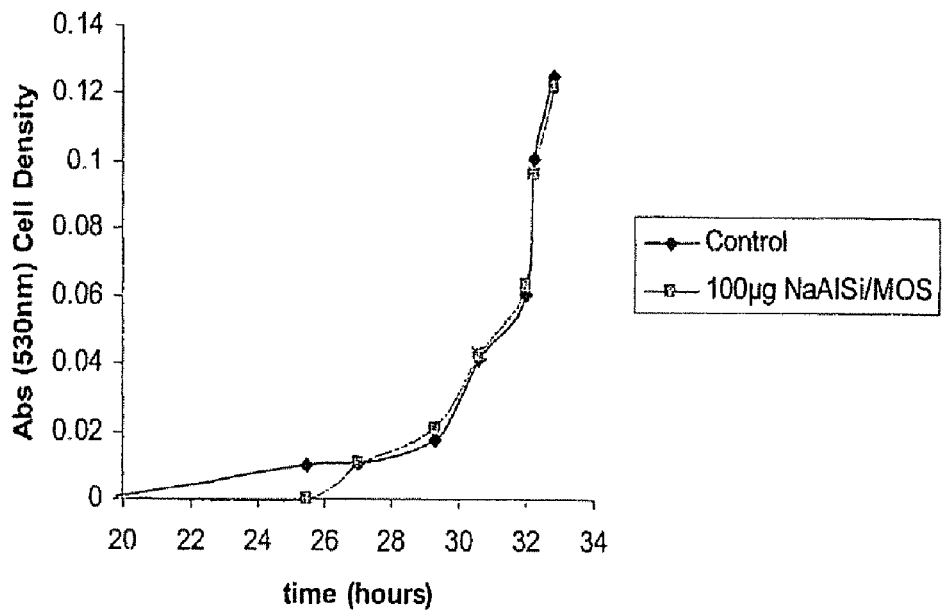
Figure 3, Puntenney and Forsberg
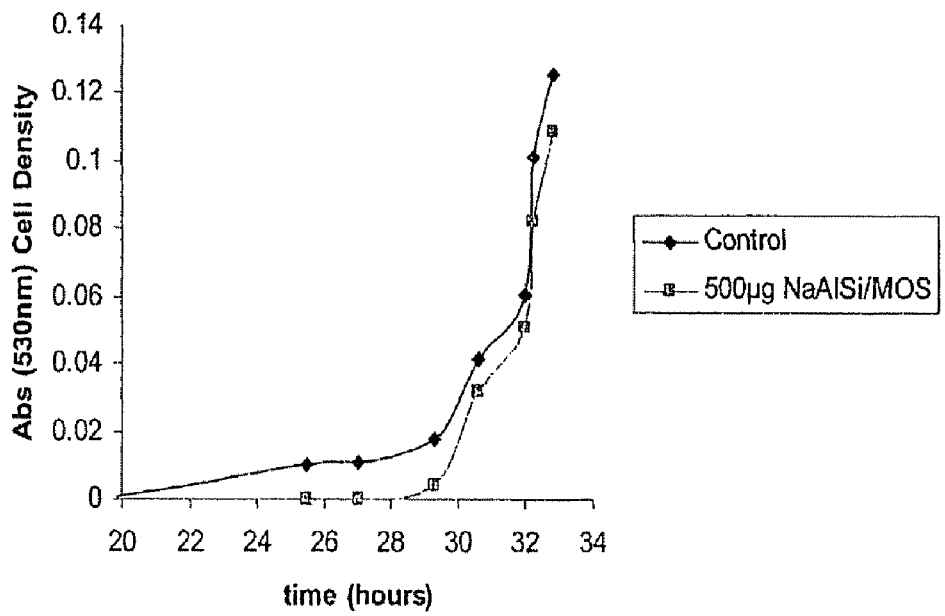

Figure 4, Puntenney and Forsberg
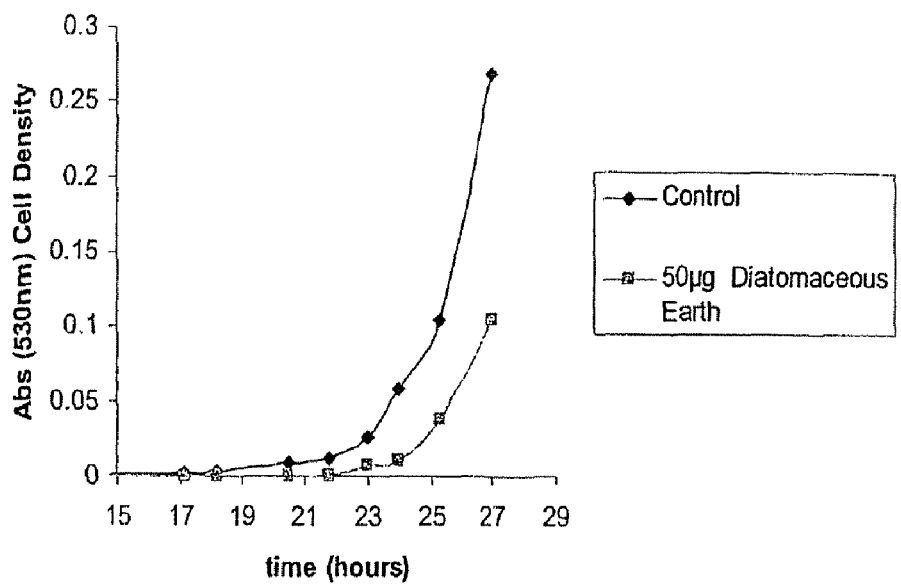
Figure 5, Puntenney and Forsberg
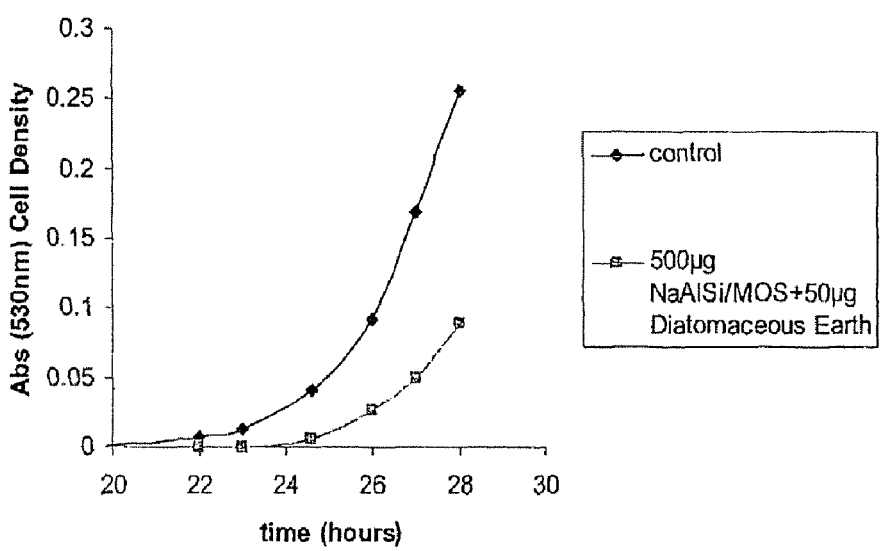

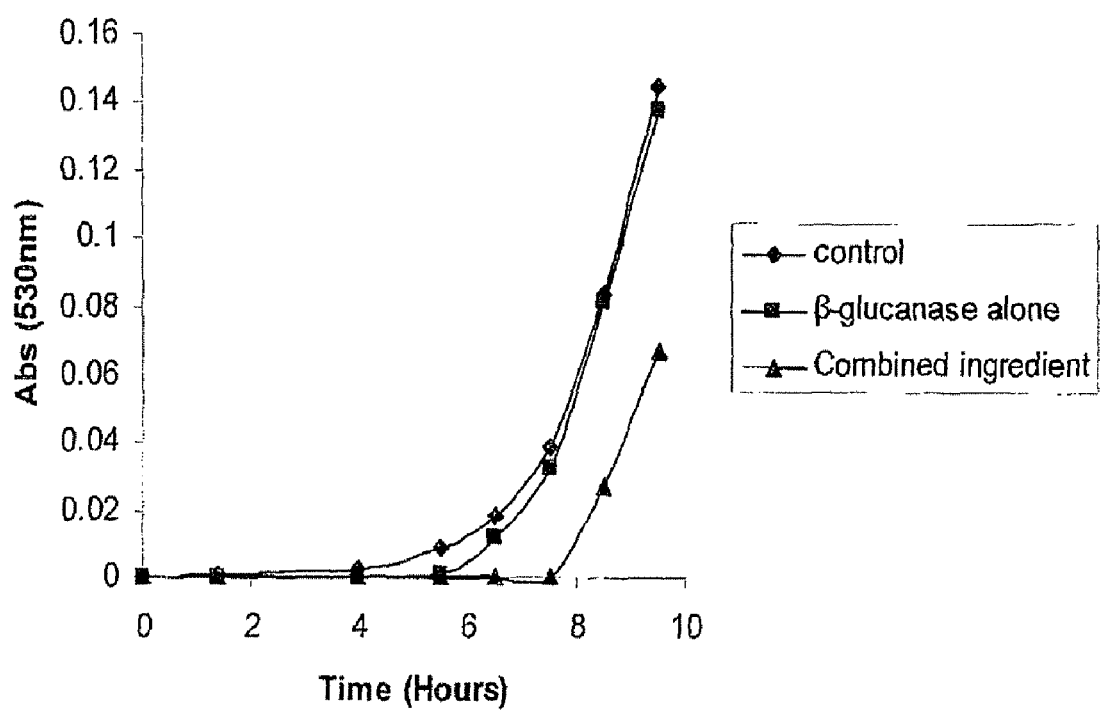
Figure 6: Puntenney and Forsberg

METHODS AND COMPOSITIONS FOR THE INHIBITION OF GROWTH OF INFECTIOUS *ASPERGILLUS FUMIGATUS* AND OTHER MYCOTIC ORGANISMS IN THE GUT OF MAMMALIAN AND AVIAN SPECIES

REFERENCE TO RELATED APPLICATION

This application is a divisional of application Ser. No. 10/388,525 filed Mar. 17, 2003 now abandoned, which claims priority from provisional application Ser. No. 60/414,828, filed Sep. 27, 2002, all of the above-mentioned applications which are incorporated herein by reference and made a part hereof.

BACKGROUND OF THE INVENTION

1. Field of the Invention

Methods and compositions for the inhibition of growth of infectious *Aspergillus fumigatus* and other pathogenic mycotic organisms in the gastrointestinal tract of mammalian and avian species.

2. Background

Aspergillosis and mycotic infections. Aspergillosis is an acute systemic mycotic infection caused by *Aspergillus* sp. Species of *Aspergillus* known to cause an infection in mammals and avian species include *Aspergillus fumigatus, Aspergillus flavis* and *Aspergillus niger*. Infectious aspergillosis has been involved in mycotic abortions and related diseases (Jensen et al., 1991; McCausland et al, 1987), Medical literature contains numerous references indicating an increasing incidence of small bowel infarctions and coagulopathies in humans related to aspergillosis (Catalano et al., 1997; Prescott et al., 1992; Oshawa, 1991). *Aspergillus fumigatus* has also been implicated as a possible etiological agent in Jejunal Hemorrhage Syndrome in cattle, a new emerging disease that causes massive hemorrhaging of the small intestine (Puntenney et al., 2003). This disease also affects immunocompromised humans Aspergillosis is also documented to cause a high incidence of abortions and pneumonia in cattle, a source of significant economic loss to the livestock industry (Puntenney et al., 2003).

Inoculation of an animal with *Aspergillus* sp, is commonly through ingestion of mold-contaminated feedstuffs due to improper storage or harvesting techniques, fecal contamination of feedstuffs from birds and rodents, and inhalation of *Aspergillus* spores from bedding material. The organism is especially effective in evasion of host animal defenses, by secretion of various lipid compounds, including fumigillin, fumitremorgin A, fumigaclavine, and gliotoxin at the infection site, impairing localized generation of complement factors C3a and C5a, thereby blocking recruitment of polymorphonuclear cells. Phagocytic cells normally follow the chemotactic gradient of complement components to the site of the infection, where engulfment and elimination of the organism from the animal occurs (Rhodes et al., 1992). The ability to sequester iron is a virulence factor for microorganisms. The binding of circulating iron to transferrin and lactoferrin, as well as the intercellular storage of iron, reduce levels of free iron below that required for microbial growth. *Aspergillus* sp, produces two major siderophores (high affinity iron binding compounds) that compete successfully with transferrin and lactoferrin to acquire iron for growth: N,N', N"-triacetylfusarinine C and ferricrocin. Proteolytic digestion of transferrin may also be utilized as a means of iron acquisition. Iron is released from transferrin at pH<6 as a result of protonation of the iron binding site generally localized at infection site (Rhodes et al., 1992).

*Aspergillus* sp. produces two serine proteinases, elastinolytic and azocollytic enzymes, which break down tissue (Tomee and Kauffman, 2000; Frosco et al., 1989). Proteinase enzyme production is tied to tissue invasiveness and facilitates entry from colonization site into the parenchyma. Hemorrhagic infarction (vascular blockage) and tissue necrosis may follow infection (Rhodes et al., 1992). After tissue invasion, dissemination via the bloodstream to other organs and the placenta occurs. Placentitis and subsequent abortions commonly result.

The fungal cell wall is composed of highly-branched β-1, 3glucans with linkages to chitin, galactomannan and a linear β-1,3/1,4 glucan (Fontaine, et al., 2000). Understanding of the structural biology of pathogenic fungi has aided the design of the invention. The efficacy of the invention is partly related to the addition of β-1,3(4)-endoglucanohydrolase, which delays initiation of fungal growth via enzymatic degradation of cell wall components.

A second component of the invention, which functions in tandem with β-1,3(4)-endoglucanohydrolase, is β-1,3 glucan. The role of β-1,3 glucan in macrophage activation and response to pathogens is well documented in the literature (Czop, et al., 1985, Xia et al., 1999). Upon entering the aqueous conditions of the digestive tract, the large glucan molecules in the invention, via the enzymatic activity of β-1, 3(4)-endoglucanohydrolase, are effectively reduced to smaller moieties that may be accepted by macrophage receptors, stimulating immunological activation. Other components of the invention, diatomaceous earth and aluminosilicate, are capable of binding toxic lipid compounds which are secreted by pathogenic fungi. These toxins, if not bound, effectively block release of complement factors required for macrophage response to colonization.

The feeding of a combination of β-1,3(4)-endoglucanohydrolase, β-glucan, calcined diatomaceous earth (hereafter identified as diatomaceous earth, $SiO_2$), glucomannan, and mineral clay, such as aluminum silicate, montmorillonite clay, bentonite or zeolite, has been shown to delay growth of *A. fumigatus* for a period of several hours in laboratory cultures and clinical trials thereby effectively minimizing the ability of *Aspergillus* to inhibit complement factor production thereby allowing an intact immune system to respond to fungal colonization.

SUMMARY OF THE INVENTION

The object of the present invention is to provide a novel and previously unknown method for inhibition of the colonization of the digestive tracts and consequent systemic infection (mycosis) of mammalian and avian species by various pathogenic microorganisms (specifically pathogenic fungal organisms). The invention may be applied to, but not limited to, in situ inhibition of the enteric growth and mycosis caused by various pathogenic microorganisms including *Aspergillus, Aureobasidium, Candida, Eupenicillium, Eurotium, Fusarium, Mucor, Penicillium, Raciborskiomyces* and other genera which comprise the fungal taxonomic classification (Kingdom Fungi) as outlined by Alexopolous et al., 1996.

A further object of this invention is to provide a method for inhibition of pathogenic microbial growth in situ and, consequently, in blood and to thereby minimize or obviate morbidities and mortalities caused by, but not limited to, pathogenic fungi with a preparation comprising a combination of β-1,3 (4)-endoglucanohydrolase, β-glucan, diatomaceous earth, glucomannan, and mineral clay, such as aluminum silicate, montmorillonite clay, bentonite or zeolite.

Another object of the invention is to provide a composition comprising a combination of β-1,3(4)-endoglucanohydrolase, β-glucan, diatomaceous earth, mineral clay, and glucomannan, which additively minimizes growth and, thereby, reduces mycotic potential of pathogenic fungi in the gastrointestinal tracts of mammalian and avian species.

Additional objects, advantages and novel features of the invention will be set forth, in part, in the description that follows and will, in part, become apparent to those skilled in the art upon examination of the following or may be learned with the practice of the invention. To achieve the foregoing and other objects, and in accordance with the purposes of the present invention as described herein, a novel method is described for the inhibition of growth of pathogenic fungal organisms which typically underlie enteric-based and mycotic morbidities and mortalities of mammalian and avian species. In particular, this invention minimizes or eliminates the colonization of the gastrointestinal tract by pathogenic fungi, reduces the populations of pathogenic organisms in blood and thereby minimizes or eliminates pathologies directly caused by and indirectly caused by this colonization. The invention comprises a mixture of β-1,3(4)-endoglucanohydrolase, β-glucan, diatomaceous earth, mineral clay, and glucomannan. The diatomaceous earth is standard commercial grade available from a variety of sources. The β-1,3(4)-endoglucanohydrolase is produced from submerged fermentation of a strain of *Trichoderma longibrachiatum*. The β-1,3(4)glucan and glucomannan are derived from a commercial product and are an extraction from any of a number of yeast organisms. The mineral clay product is a standard commercial grade (examples include, but are not limited to, montmorillonite clay, bentonite and zeolite). Extractions and productions of diatomaceous earth, yeast cell wall extract and mineral clay are well known in the art and commercially-available.

The compositions which are provided by the invention can be fed to any mammalian or avian species including, but not limited to, bovine, equine, ovine, caprine and avian species. When admixed with the feed or food or fed as a supplement, the invention minimizes or eliminates the growth of pathogenic fungi in the gut thereby allowing colonization of the gut with non-pathogenic species. The invention also minimizes or eliminates invasion of the blood compartment by pathogenic fungi. The invention thereby minimizes or eliminates the manifestations of the pathologies typically associated with enteric fungal infections. Administration of the product may be used as a prophylactic (i.e., to prevent colonization and growth of pathogenic fungal species in the gut of mammalian or avian species), as an additive to feeds or foods infected with pathogenic fungi or as a preferred method to treat and thereby minimize or eliminate an existing, diagnosed or non-diagnosed, enteric fungal infection and mycoses. Application of the invention as described herein and via the specific and novel mechanisms described herein will minimize and possibly eliminate manifestations of enteric fungal infections and, consequently, mycotic infections including, but not limited to, the following genera: *Aspergillus, Aureobasidium, Candida, Eurotium, Fusarium, Mucor, Penicillium* and *Rachiborskiomyces*. Application of the invention as described herein will also minimize or possibly eliminate manifestations associated with the presence of pathogenic fungal organisms, as identified above, in food or feed of mammalian and avian species.

DESCRIPTIONS OF THE DRAWINGS

The accompanying drawings and photographs which are incorporated into the following "Detailed Description of the Invention" form part of the specification and illustrate several aspects of the present invention and, together with the Detailed Description, serve to explain the details of the invention. In the following section:

FIG. 1 shows the effects of adding 50 μl of a mixture of 95.6% mineral clay and 4.4% β-1,3(4)glucan and glucomannan extract (40 mg/ml) on the growth of *Aspergillus fumigatus* on a Sabouraud dextrose agar plate supplemented with chloranphenicol and gentimycin.

FIG. 2 shows the effects of adding a low concentration (100 μg/10 ml culture) of a mixture of 95.6% mineral clay and 4.4% β-1,3(4)glucan and glucomannan on the growth curve of *Aspergillus fumigatus* in a Sabouraud dextrose broth supplemented with chloramphenicol and gentimycin. The x-axis represents hours of culture. The y-axis represents density of the culture measured at an absorbance of 530 nm.

FIG. 3. shows the effects of adding a high concentration (500 μg/10 ml culture) of a mixture of 95.6% mineral clay and 4.4% β-1,3(4)glucan and glucomannan on the growth curve of *Aspergillus fumigatus* in a Sabouraud dextrose broth supplemented with chloramphenicol and gentimycin. The x-axis represents hours of culture. The y-axis represents density of the culture measured at an absorbance of 530 nm.

FIG. 4. shows effects of adding diatomaceous earth (50 μg/10 ml of culture) on the growth curve of *Aspergillus fumigatus* in a Sabouraud dextrose broth supplemented with chloramphenicol and gentimycin. The x-axis represents hours of culture The y-axis represents density of the culture measured at an absorbance of 530 nm.

FIG. 5. shows the effects of adding a three-way combination of 95.6% mineral clay plus 4.4% β-1,3(4)glucan and glucomannan (500 μg/10 ml culture) and diatomaceous earth (50 μg/10 ml culture) on *A. fumigatus* growth as described for FIGS. 2-4. The x-axis represents hours of culture. The y-axis represents density of the culture measured at an absorbance of 530 nm.

FIG. 6. shows the effects of adding β-1,3(4)-endoglucanohydrolase alone (100 μg/ml of culture medium) and a combination of β-1,3(4)-endoglucanohydrolase (100 μg/ml culture medium) and 100 μg/ml of the mixture used in Experiment 6 (FIG. 5: Combined ingredient) on *A. fumigatus* growth as described for FIG. 5. The y-axis represents the density of the culture measured at an absorbance of 530 nm.

DETAILED DESCRIPTION OF THE INVENTION

The present invention is based on the novel discovery that a combination of β-1,3(4)-endoglucanohydrolase, β-1,3(4) glucan, diatomaceous earth, mineral clay, and glucomannan effectively inhibit the growth of pathogenic fungal species and thereby reduce or eliminate the direct or indirect negative consequences which accrue to the host mammalian or avian organism.

The β-1,3(4)-endoglucanohydrolase is from a commercial source and is produced from submerged fermentation of a strain of *Trichoderma longibrachiatum*.

The diatomaceous earth is prepared by methods commonly known in the art. It is available as a commercially-available acid-washed, product with 95% silica ($SiO_2$) and with its remaining components not assayed but consisting primarily of ash (minerals) as defined by the Association of Analytical Chemists (AOAC, 2002).

The yeast cell wall extract is prepared by a method commonly known in the art. It is a commercial source of β-1,3(4) glucan and glucomannan derived from primary inactivated yeast (*Saccharomyces cerevisiae*) with the following chemical composition:

| | |
|---|---|
| Moisture | 2-3% |
| Dry matter | 97-98% |
| Proteins | 14-17% |
| Fats | 20-22% |
| Phosphorous | 1-2% |
| Mannans | 22-24% |
| β-1,3 (4)glucan | 24-26% |
| Ash | 3-5% |

The mineral clays (aluminosilicates) used in this invention may be fulfilled by any of a variety of commercially-available clays including, but not limited to, montmorillonite clay, bentonite and zeolite.

In a preferred embodiment of the invention, β-1,3(4)endoglucanohydrolase, diatomaceous earth, yeast cell wall extract and mineral clay are combined at 0.05-3%, 1-40%, 1-20% and 40-92%, respectively. In a preferred composition, β-1,3 (4)-endoglucanohydrolase, diatomaceous earth, yeast cell wall extract and mineral clay are combined at 0.1-3%, 5-40%, 2-10% and 40-80%, respectively. In an especially preferred embodiment of the invention, β-1,3(4)-endoglucanohydrolase, diatomaceous earth, yeast cell wall extract and mineral clay are combined at 0.2-3%, 30-40%, 4-6% and 50-65%, respectively. The preferred physical form of the invention is a dry, free-flowing powder which is suitable for direct inclusion into a feed, food product or as a supplement to a total mixed ration or diet.

The compositions provided by the present invention may be incorporated directly into commercially-available feeds or food products or fed as supplements to commercially-available feeds or food products. The composition contained in the present invention may be fed to any mammalian or avian species. The methods of the invention comprise reducing the growth and associated mycosis caused by enteric infections of pathogenic fungal organisms in the gut of mammalian and avian species. When incorporated directly into feeds, the present invention may be added to feeds in amounts ranging from 0.1 to 5 kg per ton of feed. In an especially preferred composition, the invention may be added to feeds in amounts ranging from 1-2 kg per ton of feed.

The composition contained in the present invention may be added to animal feedstuffs or to foods in amounts ranging from 0.0125% to 2% by weight of feed. In a preferred embodiment, the composition is added to animal feedstuffs or to food in amounts from 0.0625% to 1% by weight of feed. In an especially preferred embodiment, the invention is added in amounts from 0.125% to 0.5% by weight of feed.

Alternatively, the composition contained in the present invention may be fed directly to mammalian or avian species as a supplement in amounts 0.016 grams/kg to 0.37 grams/kg of live body weight per day. In an especially preferred embodiment, the invention may be provided to mammalian and avian species in amounts of 0.10 grams/kg to 0.20 grams/kg of body weight per day. One of skill and art can appreciate that the amount of the invention fed can vary depending upon the animal species, size of the animal and type of the feedstuff to which the invention is added.

The novel methods of this invention comprise the ability of a combination of β-1,3(4)-endoglucanohydrolase, diatomaceous earth, yeast cell wall extract and clay to inhibit the enteric growth and mycosis caused by various pathogenic fungal genera which include, but are not limited to, *Aspergillus, Aureobasidium, Candida, Eurotium, Fusarium, Mucor, Penicillium* and *Rachiborskiomyces* sp. The benefits resulting from the application of the invention to mammalian species include, but are not limited to, reduced death losses, reduced incidence of mycotic abortion, reduced incidence of jejunal hemorrhage syndrome (dead gut syndrome), reduced incidence of scouring (diarrhea), improved growth rate, improved efficiency of growth, improved milk production, improved efficiency of milk production and reduced somatic cell counts in milk products (dairy animals). The benefits from the application of the invention to avian species include, but are not limited to, reduced death losses, improved growth and egg production, improved fertility, and reduced incidence of enteric diseases.

EXAMPLES

The following are intended to be illustrative of the invention, and are not to be considered restrictive of the scope of the invention as otherwise described herein.

Example 1

The following novel experiment documents the presence of mold spores or conidia in the feed, jejunal contents and jejunal wall of a Holstein dairy cow which died in 2002 from jejunal hemorrhage syndrome (dead gut syndrome).

Samples of feed, jejunal contents and jejunal tissue were homogenized in a Polytron and serial dilutions (1 ml) of these samples were applied to a Petrifilm® mold count plate. The feed sample was centrifuged following homogenization to generate a particulate fraction and a soluble fraction. The density of mold counts in each of these samples is shown in Table 1.

TABLE 1

Density of colony forming units (cfu) in feed and tissue fractions of a cow which died from jejunal hemorrhage syndrome.

| Sample | Colony forming units (cfu) |
|---|---|
| feed (supernatant fraction) | 4000 colony forming units (cfu)/g feed |
| feed (particulate fraction) | 20000 cfu/g feed |
| jejunal contents of dead cow | 100 cfu/ml gut contents |
| affected jejunal tissue | 11000 cfu/g tissue (wet weight) |

The data indicate the presence of mold in feed and the gut. Of interest, the mold sample preferentially localized into the jejunal wall, a characteristic of *Aspergillus fumigatus*. These data indicated potential for the fungal infection to underlie the etiology which led to death of the animal.

Example 2

The following experiment documents a novel discovery in which we determined that fungi can colonize the gut, invade the blood and produce a mycotic condition which can result in jejunal hemorrhage, mycotic abortion and death of dairy animals. To complete this study, several novel steps were undertaken:

The sequence of *Aspergillus fumigatus* 18S small ribosomal subunit gene was determined from existing literature (Jaeger et al., 2000) and used to design DNA primers for polymerase chain reaction (PCR) analysis of the presence of *Aspergillus* DNA in the gut, tissues and blood of cows exhibiting mycotic abortion or which had died from jejunal hemorrhage. Two sets of primers were prepared: a primary pan-fungal set which amplified all fungal DNA and a "nested set" which specifically-amplified and detected *Aspergillus* genera (Jaeger et al., 2000).

Additional primers (from the 18S gene) were designed for Sybr-Green analysis (real-time quantitative PCR) to allow for the determination of the mold DNA concentration (mold "burden") in blood of cows which had mycotic abortions or which had died from jejunal hemorrhage syndrome.

Using the DNA primers designed in Step 1 (above) we determined that cows afflicted with jejunal hemorrhage syndrome or which displayed mycotic abortions exhibited high levels of *Aspergillus* mold counts in jejunal wall and blood. Using our novel real-time Sybr-Green quantification protocol (Step 2, above) we determined that the mold burden in cows which had either died from jejunal hemorrhage syndrome or which had displayed incidence of mycotic abortion were extremely high. Control (asymptomatic) cows did not harbor fungal DNA. Instead, via sequencing, we have detected other non-pathogenic fungal species (e.g., *Cladosporium*) at low concentrations. This has led us to conclude that lower levels of *Aspergillus* infection (mycosis) result in abortion (known as "mycotic abortion") whereas exceedingly high levels result in death of the infected animal. Whether or not death results from a direct effect of fungal infection or, instead, from secondary (indirect) bacterial infections (e.g., *Clostridium* sp.) has not been determined.

Example 3

The following novel experiment illustrates the ability of a mixture of clay and β-1,3(4)glucan/glucomannan (95.6% and 4.4%, respectively) to inhibit the growth of *Aspergillus fumigatus* in culture. *A. fumigatus* culture was derived from a local corn grain sample and applied as a streak to a culture plate containing Sabouraud dextrose agar medium supplemented with chloramphenicol and gentimycin (to inhibit bacterial growth). Drops (50 μl) of sodium-aluminum silicate clay combined with β-1,3(4)glucan and glucomannan (40 mg/ml: 95.6% clay, 4.4% β-1,3(4)glucan and glucomannan) were applied to the *A. fumigatus* streaks and the growth of the mold culture was evaluated following 42 hours of culture at 27° C. The mold culture at 42 hours is shown as a zigzag pattern of white mold with spreading mycelia (see FIG. 1). Drops of the clay/β-1,3(4)glucan and glucomannan product can be seen visually as brown-colored areas on the culture dish. One such spot in FIG. 1 is indicated at the tip of a piece of white paper marked "1". Application of the clay/β-1,3(4)glucan and glucomannan product to the culture clearly and effectively diminished growth of *A. fumigatus*.

Example 4

This novel experiment shows that additions of the mineral clay, β-1,3(4) glucan and glucomannan mixture (95.6% clay, 4.4% β-1,3(4) glucan and glucomannan) effectively inhibit the growth of *Aspergillus fumigatus*. The inhibition of fungal growth with these combined ingredients, represents a portion of the mechanism of action which we submit as a mechanism of action for products in the treatment and prevention of mycotic diseases in mammalian and avian species.

*Aspergillus* was inoculated into 10 ml of Sabouraud dextrose broth supplemented with chloramphenicol and gentimycin (to inhibit bacterial growth). In addition, various amounts of a combination of mineral clay: β-1,3(4) glucan and glucomannan were added directly to cultures to establish the effects of these compounds on the growth of the *Aspergillus* culture. The density of cells was utilized as an index of *A. fumigatus* cell number and density was monitored using a spectrophotometer (wavelength was 530 nm).

In control cultures (i.e., *A. fumigatus* with no additions of the three components of the invention), we typically observed a long lag phase (see FIG. 2) where little fungal growth occurred. This was followed by a rapid, "log-phase" growth curve with maximum fungal cell density being reached after several hours. When a combination of mineral clay: β-1,3(4) glucan and glucomannan product was added to the culture, the growth of the yeast culture was delayed (see FIGS. 2 and 3). Specifically, addition of mineral clay: β-1,3(4)glucan and glucomannan mixture in combination, delayed entry of the *A. fumigatus* culture into the rapid log-phase growth. However, once *A. fumigatus* growth began, this product did not limit the total growth of the culture. The lowest effective dose of the clay: β-1,3(4)glucan and glucomannan combination was 100 μg/10 ml culture where a delay of 1-2 hours in growth was observed (see FIG. 2). Higher levels of the mineral clay: β-1,3(4)glucan and glucomannan mixture (e.g., 500 μg/10 ml) delayed entry of the *A. fumigatus* into log-phase growth (see FIG. 3).

Of interest, the transit time of digesta in an adult bovine animal is 48-72 hours. The poorer growth conditions which *A. fumigatus* would find in the bovine digestive tract (i.e., due to competition with other microbial species, less growth substrate and less oxygen) would most likely alter its growth in such a manner that a delay in log-phase growth could result in loss of the infectious organism in the feces before it has opportunity to rapidly proliferate. Hence, we propose that the delay in the log-phase fungal growth caused by the presence of a 95.6% mineral clay with 4.4% β-1,3(4) glucan and glucomannan mixture effectively reduces the degree of colonization of the gut which may be caused by *Aspergillus* and other fungal genera and thereby reduces the harmful direct, and possibly indirect, effects of an *Aspergillus* infection or infection by other pathogenic fungal species.

Example 5

This novel experiment documents the ability of diatomaceous earth to inhibit the growth of *A. fumigatus* in culture.

Similar to Example 4, diatomaceous earth was added to cultures of *A. fumigatus* which had been supplemented with chloramphenicol and gentimycin (to inhibit bacterial growth). A control sample was prepared to study fungal growth in the absence of diatomaceous earth. In addition, various levels of diatomaceous earth (5, 50, 250, 500, 1000 and 5000 μg/10 ml culture) were added to *A. fumigatus* cultures to determine its effects on fungal growth. Culture conditions were identical to those outlined in Example 4.

FIG. 4 documents the novel and surprising ability of diatomaceous earth to markedly reduce growth of a fungal culture. The lowest effective dose at which diatomaceous earth inhibited fungal growth was 50 μg/10 ml of culture medium (FIG. 4). Efficacy was also detected up to concentrations of 1000 μg/10 ml of culture medium (data not included).

Example 6

This novel experiment documents the additive ability of a 3-way combination of diatomaceous earth, mineral clay and β-1,3(4) glucan and glucomannan mixture to effectively inhibit fungal growth.

In this experiment, *Aspergillus fumigatus* was cultured as described in previous examples. The effects of adding a mixture of all three ingredients on growth of *A. fumigatus* were studied. The mineral clay, β-1,3(4)glucan and glucomannan mixture delayed entry into log phase growth (as described in Examples 2-5). Diatomaceous earth (50 μg/10 ml of culture)

in combination with mineral clay, β-1,3(4)glucan and glucomannan mixture (500 μg/10 ml culture) inhibited growth of the *Aspergillus* culture (i.e., a longer delay in entry into log-phase growth; see FIG. 5). Effects were greater than when products were added alone.

Example 7

This novel experiment documents the ability of β-1,3(4)-endoglucanohydrolase, alone and in combination with the other components of the invention, to markedly inhibit growth of *A. fumigatus* in liquid culture. In this experiment, the abilities of β-1,3(4)-endoglucanohydrolase alone (100 μg/ml) and a combination of β-1,3(4)-endoglucanohydrolase (100 μg/ml) and a mixture of diatomaceous earth, mineral clay and β-1,3(4) glucan/glucomannan (100 μg/ml) were combined and their effects on fungal growth (as described above) were assessed. The β-1,3(4)-endoglucanohydrolase alone was unable to reduce fungal growth (FIG. 6). Surprisingly, however, addition of this enzyme to the combination of diatomaceous earth, mineral clay and β-1,3(4) glucan/glucomannan caused a marked reduction in fungal growth, Specifically, initiation of fungal growth was delayed from 4 hours to over 7 hours (FIG. 6).

Summary of Examples

These results show that the composition of the invention (i.e., mineral clay, yeast cell wall extract, diatomaceous earth and β-1,3(4)endoglucanohydrolase) is capable of a previously-undescribed effect of inhibiting growth of pathogenic fungal species; species which have documented adverse effects on morbidities and mortalities of mammalian and avian species. The combination of products reduces growth of pathogenic fungi in the gut of mammalian and domestic species and thereby prevents the invasion and colonization of the blood compartment (mycosis) and represents a mixture which is flowable in easily incorporated into feed products and food products. The invention specifically prevents fungal-based septicemia and the deleterious direct and indirect effects resulting thereof. The present invention was effective in achieving its inhibitory effects under growth conditions which might be found in mammalian and avian digestive systems where nutrients, moisture, oxygen and elevated temperatures are provided by the host.

The foregoing description of the preferred embodiment of the invention has been presented for purposes of illustration and description. It is not intended to be exhaustive or to limit the invention to the precise form disclosed. Obvious modifications or variations are possible in light of the above illustrations. The embodiment was chosen and described to provide the best illustration of the principles of the invention and its practical application to thereby enable one of ordinary skill in the art to utilize the invention in various embodiments and with modifications as are suited to the particular use contemplated. All such modifications and variations are within the scope of the invention as determined by the appended claims when interpreted in accordance with the breadth to which they are fairly, legally and equitably entitled.

We claim:

1. A method for inhibiting growth of an infecting fungal species, comprising formulating a composition comprising a combination of β-glucans, β-1,3(4)-endoglucanohydrolase, diatomaceous earth, a mineral clay, and glucomannan and administering said composition to an animal selected from the group consisting of mammalian and avian species thereby inhibiting growth of an infecting fungal species in the digesta of said animal, thereby reducing susceptibility of the animal to a mycotic colonization of the digestive tract and invasive mycoses.

2. The method of claim 1, wherein the infecting fungal species includes a fungal genera selected from the group consisting of *Aspergillus, Aureobasidium, Candida, Eupenicillium, Eurotium, Fusarium, Mucor, Penicillium*, and *Rachiborskiomyces*.

3. The method of claim 1, wherein the infecting fungal species is a member of the *Aspergillus* genera.

4. The method of claim 1, wherein the infecting fungal species is *Aspergillus fumigatus*.

5. The method of claim 1, wherein the mineral clay is selected from the group consisting of montmorillonite, bentonite, aluminosilicate, zeolite clays, and mixtures thereof.

6. The method of claim 1, further including producing the β-1,3(4)-endoglucanohydrolase from submerged fermentation of *Trichoderma longibrachiatum*.

7. The method of claim 1, further including deriving the β-glucans and glucomannan from boiling and enzyme autolysis of gram positive yeast cell walls from the genera of *Saccharomyces*.

8. The method of claim 1, further including deriving the β-glucans and glucomannan from boiling and enzyme autolysis of gram positive yeast cell walls from *Saccharomyces cerevisiae*.

9. The method of claim 1, further including calcining the diatomaceous earth at a minimum temperature of 900° C.

10. The method of claim 1, wherein the composition comprises between 15% and 40% diatomaceous earth, between 50% and 81% mineral clay, between 1.0% and 5.0% β-glucans, between 0.05% and 3.0% β-1,3(4)-endoglucanohydrolase and between 1% and 8.0% glucomannan.

11. The method of claim 1, wherein the composition comprises between 20% and 30% diatomaceous earth, between 60% and 75% mineral clay, between 1.0% and 3.5% β-glucans, between 0.1% and 3.0% β-1,3(4)-endoglucanohydrolase and between 1.0% and 6.0% glucomannan.

12. The method of claim 1, further comprising admixing the composition into foods or animal feedstuffs in a concentration of between 0.0125% and 5% by weight of the composition based on the total weight of the foods or feedstuffs for the purpose of inhibiting fungal growth in feed, food or digesta.

13. The method of claim 1, further comprising admixing the composition into a food or feedstuff, and wherein said administering includes feeding said food or feedstuff to domestic livestock.

14. The method of claim 1, further comprising admixing the composition into a food or feedstuff, and wherein said administering includes feeding said food or feedstuff to ruminant livestock.

15. The method of claim 1, wherein said administering of the composition reduces mycotic colonization of the gastrointestinal tract of said animal.

* * * * *